(12) United States Patent
Stroefer et al.

(10) Patent No.: US 7,592,479 B2
(45) Date of Patent: Sep. 22, 2009

(54) REPROCESSING OF REACTION MATERIAL DISCHARGED FROM PHOSGENATION REACTORS

(75) Inventors: Eckhard Stroefer, Mannheim (DE);
Stephan Scholl, Braunschweig (DE);
Martin Sohn, Mannheim (DE);
Andreas Woelfert, Bad Rappenau (DE);
Hans-Juergen Pallasch, Ludwigshafen (DE); Jan Peter Bredehoeft, Boehl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 530 days.

(21) Appl. No.: 10/529,182

(22) PCT Filed: Sep. 18, 2003

(86) PCT No.: PCT/EP03/10381
§ 371 (c)(1),
(2), (4) Date: Mar. 24, 2005

(87) PCT Pub. No.: WO2004/031132
PCT Pub. Date: Apr. 15, 2004

(65) Prior Publication Data
US 2006/0052629 A1    Mar. 9, 2006

(30) Foreign Application Priority Data
Sep. 27, 2002   (DE) ............................... 102 45 584

(51) Int. Cl.
*C07C 263/101*    (2006.01)
(52) U.S. Cl. ...................................... 560/352; 560/330
(58) Field of Classification Search ................. 560/352, 560/330
See application file for complete search history.

(56) References Cited

U.S. PATENT DOCUMENTS

| 3,140,305 A |   | 7/1964  | Lowenstein |         |
|-------------|---|---------|------------|---------|
| 3,219,678 A | * | 11/1965 | Kober et al. | 560/352 |
| 3,471,543 A |   | 10/1969 | Sayigh     |         |
| 3,892,634 A |   | 7/1975  | Hajek et al. |       |
| 4,118,286 A |   | 10/1978 | Burns et al. |       |
| 5,962,728 A |   | 10/1999 | Keyvani et al. |     |

FOREIGN PATENT DOCUMENTS

| FR | 1 487 546 | 7/1967 |
| GB | 1 083 910 | 9/1967 |
| RO | 61 695    | 9/1976 |

\* cited by examiner

*Primary Examiner*—James O. Wilson
*Assistant Examiner*—Ebenezer Sackey
(74) *Attorney, Agent, or Firm*—Oblon, Spivak, McClelland, Maier & Neustadt, P.C.

(57) ABSTRACT

Isocyanates are prepared by reacting primary amines with phosgene in a reactor by a process in which a reaction discharge is present in the form of a suspension which contains the isocyanate to be prepared, as a liquid, and carbamyl chlorides as a solid, and the suspension is worked up in a film evaporator, and this process is carried out in a production plant.

10 Claims, 2 Drawing Sheets

US 7,592,479 B2

REPROCESSING OF REACTION MATERIAL DISCHARGED FROM PHOSGENATION REACTORS

CROSS REFERENCE TO RELATED APPLICATIONS

This application is U.S. national stage of International Application No. PCT/EP03/10381, filed Sep. 18, 2003. This application claims priority to German Application No. 102 45 584.8, filed Sep. 27, 2002.

BACKGROUND

The present invention relates to a process for the preparation of isocyanates by reacting primary amines with phosgene in a reactor, the reaction discharge being present in the form of a suspension which contains the isocyanate to be prepared, as a liquid, and carbamyl chlorides as a solid, and working up the suspension in a film evaporator, and a production plant for carrying out this process.

Numerous processes for the preparation of isocyanates by reacting primary amines with phosgene are known. For example, U.S. Pat. No. 3,140,305 describes a process for the preparation of substantially pure aromatic diisocyanate by reaction of amines with phosgene and subsequent distillation of the reaction products.

It is furthermore known that the use of a large excess of phosgene relative to the amino groups used leads to high selectivities with respect to the isocyanate prepared and may thus have a decisive effect on the cost-efficiency of the process. However, the phosgene hold-up of the plant increases with increasing ratio of phosgene to amino groups, a very short phosgene hold-up of the plant being desirable owing to the toxicity of phosgene.

SUMMARY

It is an object of the present invention to provide a process for the preparation of isocyanates which makes it possible to carry out the reaction with very small losses of yield in combination with a very short phosgene hold-up.

We have found that this object is achieved if the reaction discharge from the phosgenation reactor, which is present in the form of a suspension which contains the isocyanate to be prepared, as a liquid, and carbamyl chlorides as a solid is transferred to a film evaporator for working up. The achievement of the object was surprising for a person skilled in the art since there have to date been considerable reservations against the use of solids in film evaporators, in particular in thin-film evaporators.

The present invention relates to a process for the preparation of isocyanates by reacting primary amines with phosgene in a reactor, the reaction discharge being present in the form of a suspension which contains the isocyanate to be prepared, as a liquid, and carbamyl chlorides as a solid, wherein the suspension is worked up in a film evaporator.

The present invention furthermore relates to the use of film evaporators for working up reaction discharges from phosgenation reactors, the reaction discharges being present in the form of a suspension which contains the isocyanate to be prepared, as a liquid, and carbamyl chlorides as a solid.

Finally, the present invention relates to a production plant for the production of isocyanates by reacting primary amines with phosgene, comprising a reactor in which the reaction of primary amines with phosgene takes place and at least one film evaporator to which the reaction discharge of the reactor, which is present in the form of a suspension which contains the isocyanate to be prepared, as a liquid, and carbamyl chlorides as a solid, is fed.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF EXEMPLARY EMBODIMENTS

Figure 1:
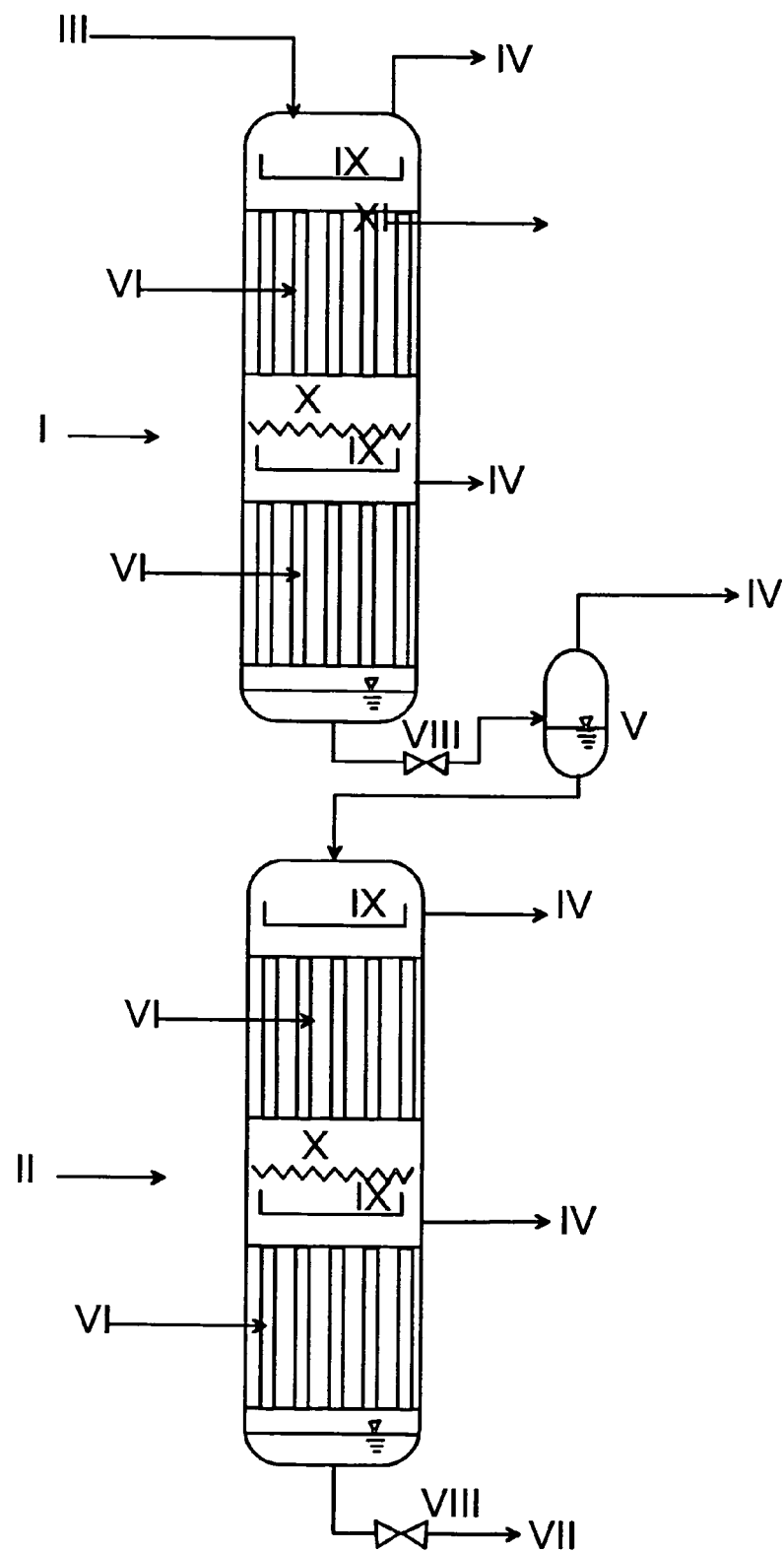
FIG. 1 is a schematic depiction of falling-film evaporators that may be employed to practice exemplary processes according to the present invention.

Any desired primary amine or a mixture of two or more of these amines can be used for the novel process. Aromatic amines, in particular those of the diaminodiphenylmethane series or the higher homologs thereof, are preferably used. Examples are methylenediphenylamine (MDA; individual isomers, isomer mixture and/or oligomers thereof), toluenediamine (TDA), n-pentylamine, 6-methyl-2-heptanamine, cyclopentylamine, R,S-1-phenylethylamine, 1-methyl-3-phenylpropylamine, 2,6-xylidine, 2-(N,N-dimethylamino)ethylamine, 2-(N,N-diisopropylamino)ethylamine, C11-neodiamine, 3,3'-diaminodiphenyl sulfone and 4-aminomethyl-1,8-octandiamine. MDA and TDA are preferably used. The process can also be used for aliphatic amines. The use for 1,6-diaminohexane and for isophoronediamine is preferred here.

The novel process is accordingly suitable for the preparation of any desired isocyanates. The process can be particularly advantageously used for the preparation of methylene (diphenyl diisocyanate) (MDI) and tolylene diisocyanate (TDI).

In the preparation of isocyanate by reacting a primary amine with phosgene, carbamyl chlorides are formed as intermediates in a first fast step according to the following equation, which carbamyl chlorides decompose to isocyanates and HCl in a rate-determining, slow step in an equilibrium reaction:

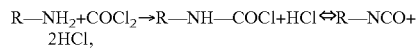

where R is an organic radical.

Furthermore, the hydrogen chloride formed can react with amines to give amine hydrochlorides ($R-NH_3^+Cl^-$).

The reaction of phosgene with diamine is carried out in the novel process in a reactor. This may be any conventional reactor which is known from the prior art and is suitable for phosgenation, preferably for continuous phosgenation, and withstands the customary pressures. Suitable materials are, for example, metals, such as steel, silver or copper, glass, ceramic or homogeneous or heterogeneous mixtures thereof. Steel reactors are preferably used.

The reactor designs known from the prior art can generally be used. Tubular reactors, columns and stirred kettles are preferably used.

In the novel process, the mixing of the reactants (amine and phosgene) is carried out in a mixing apparatus which permits high shearing of the reaction stream passed through the mixing apparatus. A preferably used mixing apparatus is a rotation mixing apparatus, a mixing pump or a mixing nozzle, which is located upstream of the reactor. A mixing nozzle is particularly preferably used.

The novel process comprises continuous, semicontinuous and batchwise processes. Continuous processes are preferred.

The reaction of amine with phosgene can be carried out in the liquid phase or in the gas phase. The reaction conditions, for example pressure and temperature, are generally parameters known from the prior art.

The novel process is preferably carried out in the liquid phase.

In a reaction of amine with phosgene in the liquid phase, an inert solvent can be added to the novel process. This inert solvent is usually an organic solvent or a mixture thereof. Chlorobenzene, dichlorobenzene, trichlorobenzene, toluene, hexane, diethyl isophthalate (DEIP), tetrahydrofuran (THF), dimethylformamide (DMF), benzene and mixtures thereof are preferred. Chlorobenzene is particularly preferred. The inert solvent can preferably be added to the amine at the beginning of the reaction. The inert solvent is usually used in an amount of from 5 to 1 000, preferably from 50 to 500, % by weight, based on the amount of amine used.

The reaction mixture emerging from the reactor (reaction discharge) is present in the form of a suspension. The suspension contains the isocyanate to be prepared, as a liquid, and still undecomposed carbamyl chlorides as solids. The suspension emerging from the reactor may furthermore contain amine hydrochlorides and/or ureas (R—NH—CO—NH—R) as solids.

Usually, carbamyl chlorides are present in an amount of from 0.01 to 35, preferably from 0.02 to 30, % by weight, based on the amount of the isocyanate to be prepared, in the suspension (reaction discharge). The carbamyl chloride is generally present in an amount of from 5 to 35, preferably from 15 to 30, % by weight, based on the amount of the isocyanate to be prepared, in the preparation of MDI. In the preparation of TDI, the carbamyl chloride is generally present in an amount of from 0.01 to 30, preferably from 0.02 to 20, % by weight, based on the amount of the isocyanate to be prepared.

Furthermore, amine hydrochlorides are generally present in an amount of from 0.01 to 10, preferably from 0.1 to 5, particularly preferably from 0.5 to 3, % by weight, based on the amount of the isocyanate to be prepared, in the suspension (reaction discharge).

Finally, ureas are generally present in an amount of from 0.05 to 15, preferably from 0.5 to 10, particularly preferably from 1 to 5, % by weight, based on the amount of the isocyanate to be prepared, in the suspension (reaction discharge).

In the context of this invention, film evaporators are understood as meaning all apparatuses in which the liquid phase of the medium to be vaporized is applied as a film (the film evaporator then corresponds to a thin-film evaporator) over the heating surface and is transported along said surface without backmixing for the purpose of vaporization. The film is bounded on one side by the heating surface and on the other side by the gaseous phase. The falling-film evaporator and the thin-film evaporator are examples of film evaporators.

Usually, the liquid or suspension to be vaporized in the film evaporator has a film thickness of from 0.01 to 10 mm, preferably from 0.1 to 6 mm, particularly preferably from 0.5 to 3 mm.

In a possible embodiment, the film evaporators used may be thin-film evaporators. Thin-film evaporators are known in the prior art and are described, for example, in Ullmanns Enzyklopädie. In general, thin-film evaporators serve for vaporizing thermally sensitive substances from high-boiling residues and for concentrating thermally labile substances, a liquid being applied as thin films to heated surfaces by allowing it to trickle down or by the action of centrifugal force, wipers or the like.

Examples of suitable thin-film evaporators are apparatuses in which the liquid film is produced mechanically, for example SAMBAY and LUWA thin-film evaporators and Sako thin-film evaporators and ALFA-LAVAL centritherm evaporators.

In a preferred embodiment, film evaporators which have no moving parts are used. Examples of these are falling-film evaporators (also referred to as downflow evaporators) and helical tube evaporators.

In this invention, the film evaporators used are preferably falling-film evaporators. The heat transfer surface may be in the form of tubes or plates. Cylindrical tubes are preferably used.

The film evaporator used in the novel process, preferably the falling-film evaporator used, is usually operated at from 0.5 mbar to 25 bar, preferably from 0.5 to 20, particularly preferably from 1 to 18, bar.

If the isocyanate to be prepared is TDI, the film evaporator used in the novel process, preferably the falling-film evaporator used, is operated at from 0.5 mbar to 25 bar, preferably from 0.5 to 20, particularly preferably from 1 to 18, in particular from 2 to 17, bar.

If the isocyanate to be prepared is MDI, the film evaporator used in the novel process, preferably the falling-film evaporator used, is operated at from 0.5 mbar to 25 bar, preferably from 0.5 to 20, particularly preferably from 1 to 18, in particular from 1.5 to 10, bar.

The temperature in the film evaporator is usually from 30 to 300° C., preferably from 50 to 200° C.

The residence time of the liquid to be vaporized depends on the temperature established. Usually, the residence time in the film evaporator is from 5 seconds to 20 minutes, preferably from 20 seconds to 10 minutes, particularly preferably from 40 to 400 seconds. For achieving the desired residence time, it may be expedient to connect two or more, preferably two, film evaporators in series. The abovementioned residence times are then based on the sum of the residence times in the film evaporators connected in series.

The suspension phase and the liquid phase may flow cocurrent or countercurrent. Liquid and gaseous phases are preferably transported countercurrent in the film evaporator used.

In a possible embodiment, the suspension (reaction discharge) is worked up in two, or if required more than two, film evaporators arranged in series. In a preferred embodiment, the two film evaporators arranged in series operate at different pressure levels.

In a preferred embodiment, two film evaporators are used, the first film evaporator operating at from 0.5 to 25, preferably from 0.5 to 20, particularly preferably from 1 to 18, bar and the second film evaporator operating at a pressure which is from 0.01 to 1, preferably from 0.02 to 0.5, particularly preferably from 0.05 to 0.2, bar lower than the pressure of the first film evaporator.

If more than two film evaporators are connected in series, the first film evaporator operates at from 0.5 to 25, preferably from 0.5 to 20, particularly preferably from 1 to 18, bar and each further film evaporator has a pressure which is in each case from 0.01 to 1, preferably from 0.05 to 0.2, bar lower than the pressure of the preceding film evaporator.

A preferred design for the use of film evaporators in the working up of reaction discharges is shown in FIG. 1:

FIG. 1 shows two falling-film evaporator units I and II arranged in series. In FIG. 1:

I is the first falling-film evaporator
II is the second falling-film evaporator
III is the feed of the reactor discharge
IV is the removal of the gas phase
V is a phase separation container
VI is a tube bundle with jacket heating
VII is the removal of the desired product (liquid)
VIII is a pressure reducing means
IX is a liquid distributor
X is a liquid collector Falling-film evaporator I operates at >0.5, preferably from 1 to 5, bar absolute; II operates at a pressure which is below that of I but is preferably >3 mbar, very particularly preferably >50 mbar.

The suspension-like reaction discharge is added to the top of I. Before addition to the top of I, the reaction discharge is, if required, passed again through a pressure reducing means, preferably a pressure reducing valve, and fed to a phase separation container in order to reduce the pressure to the operating pressure of I. After addition to the top of I, the suspension taken from the phase separation container first enters a distributor, for example a perforated box distributor, and is distributed there over tubes of a tube bundle.

The tubes have an external diameter of from 10 to 200 mm, preferably from 25 to 80 mm. The length of the tubes is from 0.5 to 15 m, preferably from 3 to 9 m. The number of tubes per falling-film evaporator is usually from 10 to 10 000, preferably from 100 to 1 000, tubes.

The tubes have, for example, an external diameter of 38 mm, a wall thickness of 2.3 mm and a length of 6 000 mm. For example, about 560 tubes are present. The suspension is collected at the lower exit of the tubes and is fed to a further distributor. Another tube bundle follows, as stated above.

At the lower part of this tube bundle is a level regulator from which the suspension is fed via a valve to an expansion vessel for pressure adaptation to II. II is designed analogously to I.

The primarily liquid suspension phase has a residence time of about 10 seconds in each unit comprising distributor and tube bundle. This results in a total residence time of about 4×10 seconds=40 seconds. By means of surface structuring, the residence time of solids can be increased by a factor of about three relative to the purely liquid phase. This gives a maximum residence time of the units I and II together of about 2 minutes.

Within a residence time of 40 seconds, carbamyl chlorides can be reduced at a wall temperature of 150° C. from an initial content of from 0.1 to 0.01% by weight to 1 ppm, based on the initial amount of carbamyl chloride. As a result of the surface structuring, even a reduction of from 10-0.1% by weight to 1 ppm is possible.

The liquid phase is then fed to a further working up, which may differ depending on the isocyanate prepared. In general, the inert solvent is separated off in the next step. This can be effected in a column or once again in a film evaporator, preferably a falling-film evaporator.

In a preferred embodiment, the distillation column is connected downstream of the one film evaporator used or of the plurality of film evaporators used.

In the film evaporators, the main cleavage of the isocyanate takes place with simultaneous phosgene separation. According to the invention, cleavage with a low phosgene hold-up is achieved by using the film evaporator. The final conversion of the carbamyl chloride, which requires a relative long time, is then achieved by adding the already phosgene-poor solution to the distillation column, in which hold-up and hence residence time are adequately produced without a greater additional phosgene hold-up. The isocyanate solution is taken off at the bottom of the distillation column, and the HCl formed in the remaining cleavage, and the remaining phosgene, are taken off at the top of the distillation column.

With the use of a plurality of film evaporators, the distillation column is usually connected downstream of the film evaporator arranged as the last one in the process sequence.

The gas phases removed, which mainly comprise HCl and phosgene and to a lesser extent solvent and traces of the isocyanate, are fed to a further working up, HCl and phosgene being separated. Any traces of isocyanate and/or solvent remain in the phosgene. The phosgene is recycled into the reaction part.

The novel process is carried out in a production plant which comprises a reactor, in which the reaction of primary amines with phosgene takes place, and at least one film evaporator to which the reaction discharge of the reactor is fed, which discharge is present in the form of a suspension which contains the isocyanate to be prepared, as a liquid, and carbamyl chlorides as a solid.

In addition to reactor and film evaporator, the production plant generally furthermore comprises the reaction stages known from the prior art, for example storage containers, mixing apparatuses and working-up stages.

Figure 2:
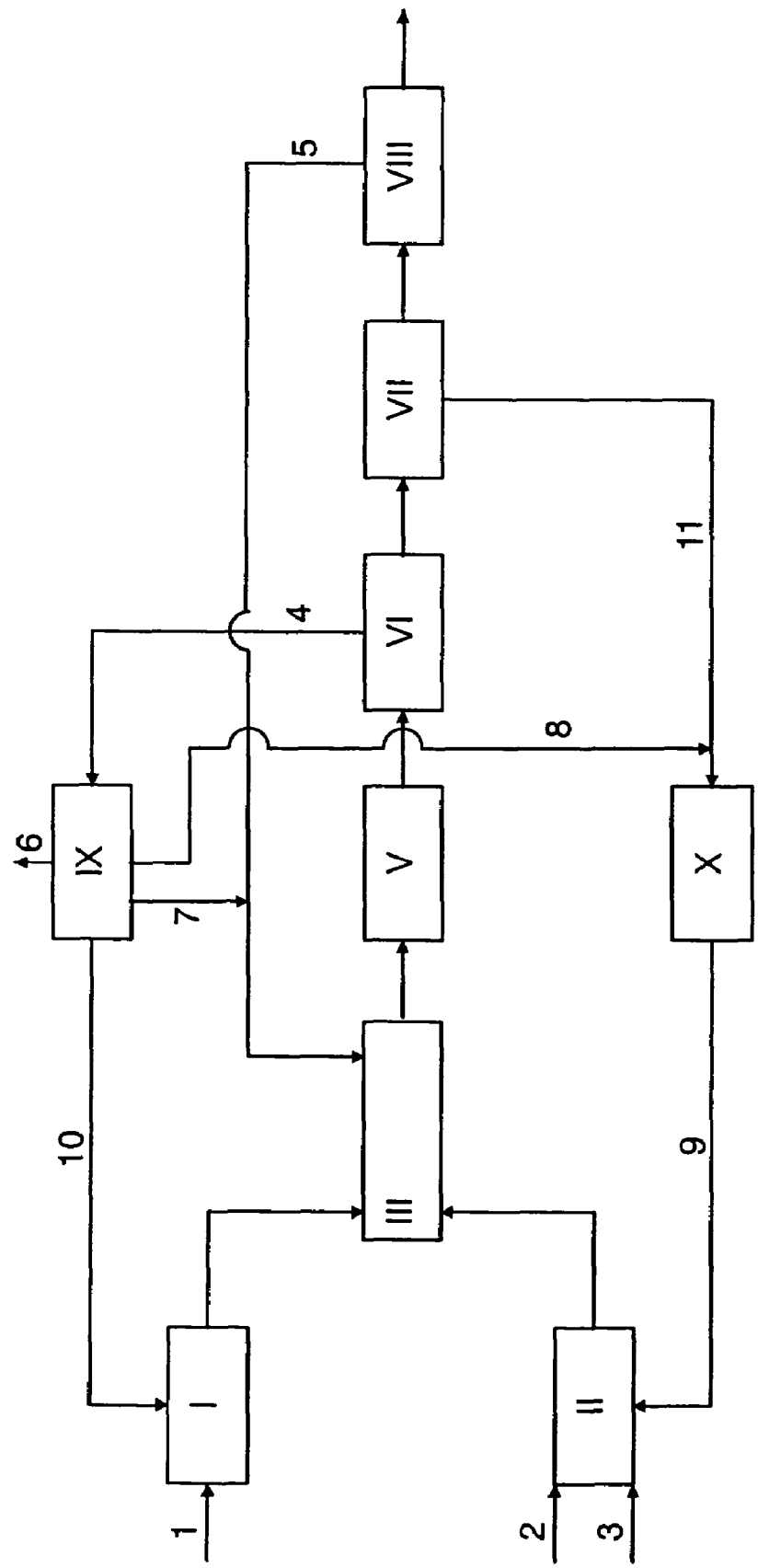
FIG. 2 is a schematic depiction of an exemplary production plant that may be employed to practice exemplary processes according to the present invention.

A preferred embodiment of a novel production plant is to be explained in more detail on the basis of a general process diagram according to FIG. 2. In FIG. 2:

I is a phosgene vessel
II is an amine vessel
III is a mixing apparatus
V is a reactor
VI is a film evaporator
VII is a second working-up apparatus
VIII is an isocyanate vessel
IX is a phosgene working-up
X is a solvent working-up
1 is the phosgene feed
2 is the amine feed
3 is the feed of inert solvent
4 is the hydrogen chloride and inert solvent separated off
5 is a recycled isocyanate stream (optional)
6 is the discharged hydrogen chloride
7 is the isocyanate separated off
8, 11 are inert solvent which has been separated off
9 is worked-up inert solvent
10 is worked-up phosgene The amine from the amine vessel II and phosgene from the phosgene vessel I are mixed in a suitable mixing apparatus III. In an optional embodiment, the mixture of amine and phosgene is additionally mixed with recycled isocyanate as solvent. After the mixing, the mixture is transferred to a reactor V. Apparatuses which are both mixing apparatus and reaction apparatus can also be used, for example tubular reactors having flange-connected nozzles.

Working-up apparatus VI is a film evaporator in one of the embodiments described above. Usually, hydrogen chloride and any inert solvent and/or small amounts of the isocyanate stream are separated off here from the isocyanate stream.

Working-up apparatus VII is a conventional distillation unit or a further film evaporator. In the second separation apparatus VII, inert solvent is preferably separated off and then worked up (X) and recycled to the amine vessel II.

In addition to the novel process and the novel production plant, the present invention furthermore relates to the use of film evaporators for working up reaction discharges from phosgenation reactors, the reaction discharges being present in the form of a suspension which contains the isocyanate to be prepared, as a liquid, and carbamyl chlorides as a solid. Accordingly, the preferred embodiments described above for the process and the production plant apply to the novel use.

The use of film evaporators for working up reaction discharges from phosgenation reactors leads to the following advantages:

The phosgene hold-up of the entire plant is permanently reduced, which is a substantial safety feature.

A production plant can be designed so that the individual slim apparatuses are individually chambered and housing of the entire plant can be dispensed with.

The capital costs are reduced, i.e. the cost efficiency increases.

The film evaporator has the following functions:

Gentle vaporization of phosgene and HCl.

Provision of flow substantially free of backmixing and with superposition of chemical reactions, in particular the decomposition of the carbamyl chloride into the desired product isocyanate and HCl.

Introduction of heat of evaporation and heat of reaction.

Substantial decrease in concentration of phosgene, HCl, suspended solids and dissolved reactants (from about 0.5% to 0.01 ppm).

EXAMPLE

Working-up of Reaction Discharges from Phosgenation Reactors

A stream III of the mixture of phosgene with a toluenediamine solution in monochlorobenzene having a mass flow rate of 0.111 kg/s was passed in liquid form from above into a first falling-film evaporator tube VI having an internal diameter of 1.5 inches and a length of 4 m, after the gas phase formed during mixing had been separated off. The stream had a temperature of T=70° C. It contains 36% by mass of phosgene, 46% by mass of MCB, 17% by mass of carbamyl chloride and 1% by mass of HCl. At a pressure of 4.5 bar absolute (abs), a thermal power of about 8.5 kilowatt (kW) was transmitted via the casing to the falling-film evaporator tube. Vapor phase and liquid phase are passed countercurrently. The liquid phase was collected in a collector X and fed from above to a second falling-film evaporator tube VI having the same dimensions as the first falling-film evaporator tube. Here too, a thermal power of about 8.5 kW was transmitted at 4.5 bar (abs). Vapor phase and liquid phase are passed countercurrently. The vapor phase of the second falling-film evaporator tube was not passed through the first falling-film evaporator tube. The liquid phase which was taken off from the second falling-film evaporator tube contained, at a temperature of T=140° C., 8% by mass of phosgene, 66% by mass of monochlorobenzene, 12% by mass of TDI and 13% by mass of carbamyl chloride and was then let down to 2.5 bar through a valve VIII into the container V. The liquid take-off from container V was fed to a third falling-film evaporator tube VI having a length of 6 m and an internal diameter of 1.5 inches, for further working-up. At a pressure of 2.5 bar (abs), a thermal power of about 3.9 kW was transmitted to the falling-film evaporator tube. Vapor phase and liquid phase were passed countercurrently. The liquid phase taken off at the bottom was collected in the collector X and fed from above to a fourth falling-film evaporator tube VI having a length of 6 m and a diameter of 1.5 inches. At a pressure of 2.5 bar (abs), a thermal power of about 3.9 kW was transmitted to the falling-film evaporator tube. Vapor phase and liquid phase are passed countercurrently. The vapor phase of the fourth falling-film evaporator tube is not passed through the third falling-film evaporator tube. The liquid discharge from the fourth falling-film evaporator tube still contained, at a temperature of T=160° C., 0.5% by mass of phosgene, 68% by mass of MCB, 27% by mass of TDI and 3% by mass of carbamyl chloride. The liquid discharge was first fed by the conventional methods for distillative phosgene removal in a distillation column and then further worked up by distillation to give pure TDI. In the distillation column for phosgene removal, the remaining carbamyl chloride also decomposed into TDI and HCl.

We claim:

1. A process for preparing an isocyanate, comprising:
reacting a primary amine with phosgene in a reactor; and
working up a reaction discharge from the reactor in a film evaporator;
wherein the reaction discharge from the reactor comprises a suspension including the isocyanate as a liquid and a carbamyl chloride as a solid.

2. The process as claimed in claim 1, wherein the film evaporator is an apparatus which has no moving parts.

3. The process as claimed in claim 1, wherein the film evaporator is a falling-film evaporator.

4. The process as claimed in claim 1, further comprising subjecting a discharge from the film evaporator to distillation in a distillation column.

5. The process as claimed in claim 1, wherein working up the reaction discharge comprises working up the reaction discharge in at least a first film evaporator and a second film evaporator, which are arranged in series and operate at different pressure levels.

6. The process as claimed in claim 5, wherein:
the first film evaporator operates at a pressure of from 0.5 to 25 bar; and
the second film evaporator operates at a pressure of from 0.01 to 1 bar lower than the pressure of the first film evaporator.

7. The process as claimed in claim 1, wherein the carbamyl chloride is present in the suspension in an amount of from 0.01 to 35% by weight, based on a weight of the isocyanate to be prepared.

8. The process as claimed in claim 1, wherein the suspension further comprises amine hydrochloride and urea.

9. A production plant comprising
a reactor wherein a primary amine is reacted with phosgene and
at least one film evaporator wherein a reaction discharge of said reactor, which is present in the form of a suspension comprising said isocyanate, as a liquid, and a carbamyl chloride, as a solid, is fed.

10. A method for working up a reaction discharge from a phosgenation reactor, the method comprising:
working up the reaction discharge from the phosgenation reactor in a film evaporator; wherein the reaction discharge comprises a suspension including the isocyanate as a liquid and a carbamyl chloride as a solid.

* * * * *